United States Patent [19]

Avant et al.

[11] Patent Number: 5,047,039
[45] Date of Patent: Sep. 10, 1991

[54] METHOD AND APPARATUS FOR EFFECTING DORSAL VEIN LIGATION AND TUBULAR ANASTOMOSIS AND LAPAROSCOPIC PROSTATECTOMY

[75] Inventors: Odis L. Avant, 4703 89th St., Lubbock, Tex. 79423; Duane A. Crawford, Lubbock, Tex.

[73] Assignee: Odis Lynn Avant, Lubbock, Tex.

[21] Appl. No.: 582,635

[22] Filed: Sep. 14, 1990

[51] Int. Cl.⁵ ............... A61B 17/00; A61M 29/00
[52] U.S. Cl. .................. 606/148; 606/153;
606/192; 128/898; 604/96; 604/104; 604/43
[58] Field of Search ........... 606/148, 151, 153, 192;
128/898; 604/96, 97, 98, 104, 43

[56] References Cited

U.S. PATENT DOCUMENTS

| | | | |
|---|---|---|---|
| 2,547,758 | 4/1951 | Keeling | 604/43 |
| 4,532,926 | 8/1985 | O'Holla | |
| 4,752,024 | 6/1988 | Green et al. | 227/19 |
| 4,848,367 | 7/1989 | Avant et al. | 128/898 |
| 4,873,977 | 10/1989 | Avant et al. | 604/96 |
| 4,911,164 | 3/1990 | Roth | 606/148 |

Primary Examiner—Stephen C. Pellegrino
Assistant Examiner—Gary Jackson
Attorney, Agent, or Firm—Mason, Fenwick & Lawrence

[57] ABSTRACT

A ligator assembly comprising a hollow, two-piece, bullet-shaped case dimensioned to be inserted in and through a body member, a pair of suture needles carried by the case, and a suture affixed to the needles. The case is provided with a pair of guide tubes for retaining the needles and guiding them out through a substantially transverse slot at the end of the case. A drive mechanism is also provided for remotely driving the needles longitudinally out of the case through the slot. The case is selectively connectable to an elongated tubular operator for placement of the ligator assembly. Apparatus for effecting an anastomosis comprises female and male connector components usable with an operator, an inflatable anvil assembly, and a connector actuator and which include mutually facing clamping surfaces for clamping generally annular tissue portions of the first and second body members together. The female connector component includes a plurality of resilient legs having bores extending therethrough. The legs are movable between a retracted position when the inflatable anvil is contracted and a distended position when the anvil is expanded. The male connector component is received by the connector actuator and includes a plurality of posts for piercing the annular tissue portions in response to actuation of the connector actuator and for matingly engaging the bores in the female connector component when the legs are in the distended position.

21 Claims, 7 Drawing Sheets

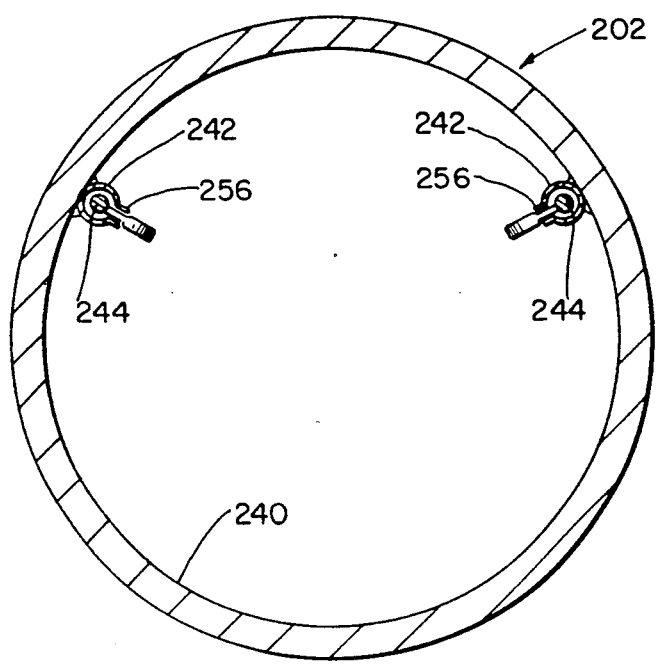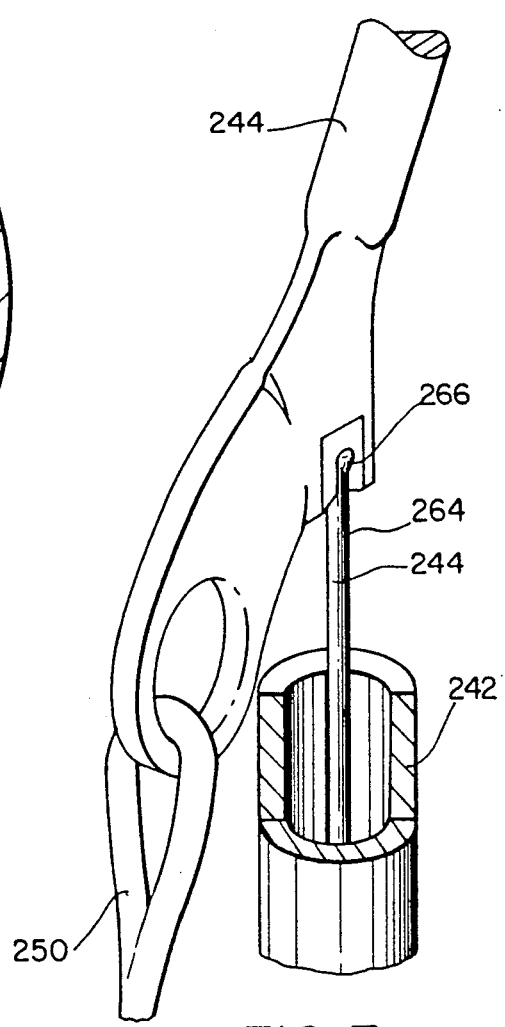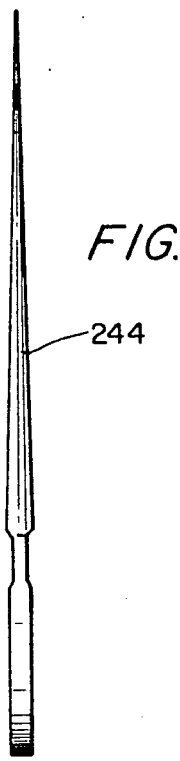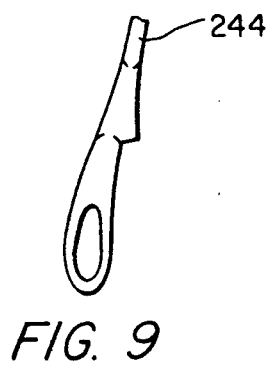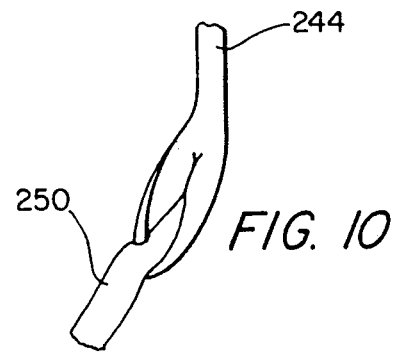
FIG. 6
FIG. 7
FIG. 8
FIG. 9
FIG. 10

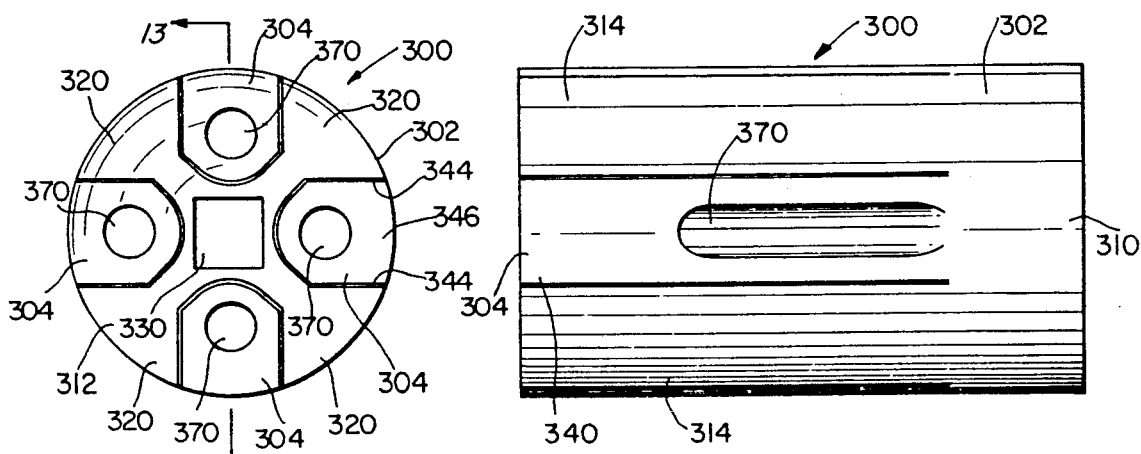
FIG. 11
FIG. 12
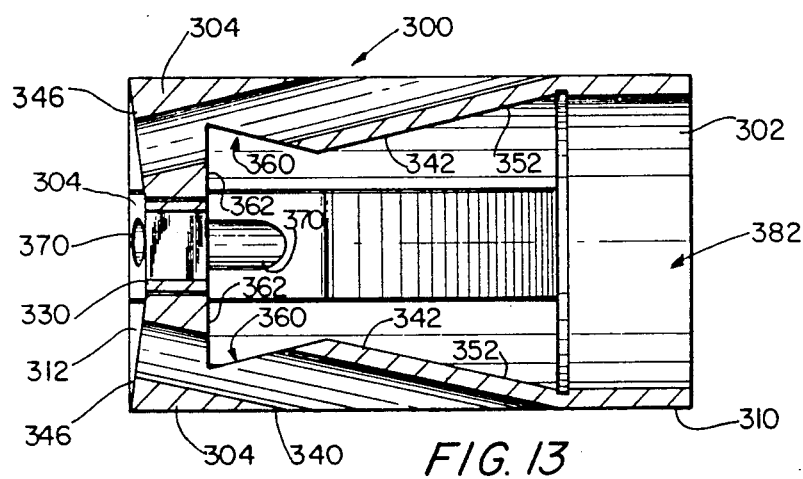
FIG. 13
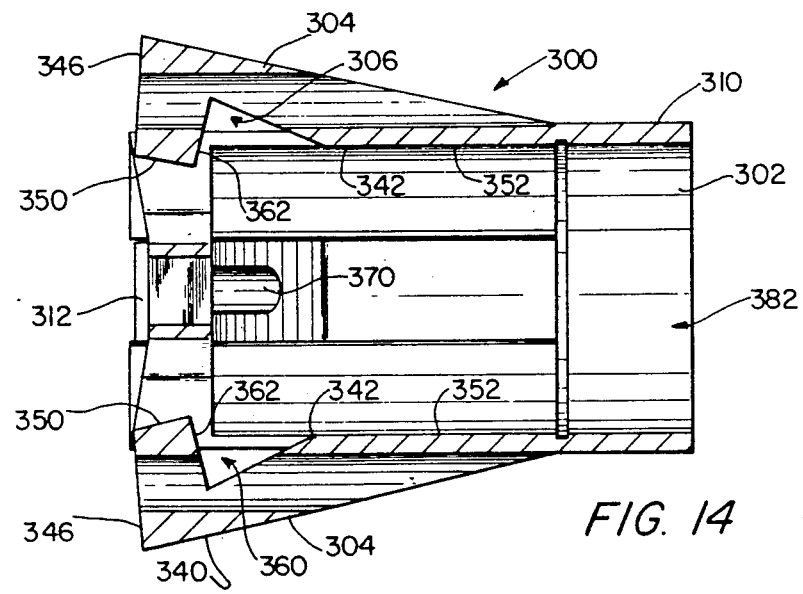
FIG. 14

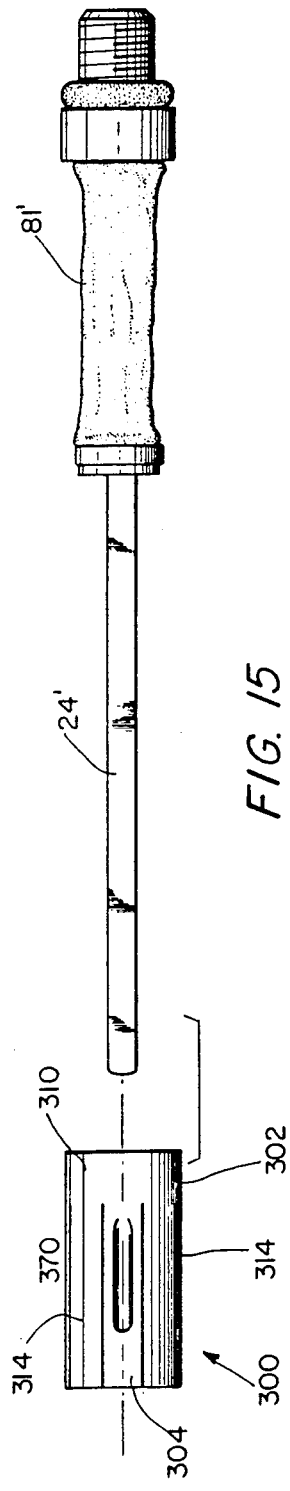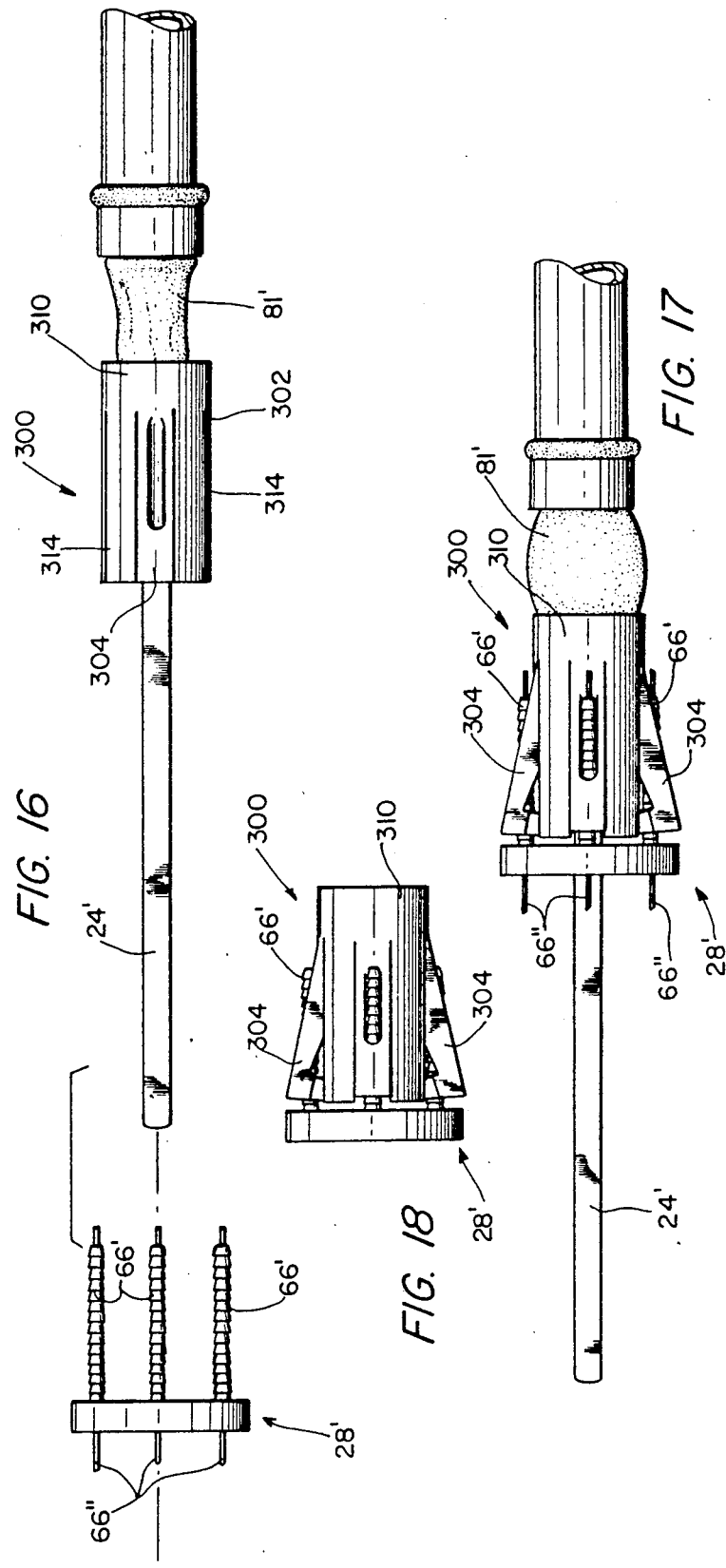

METHOD AND APPARATUS FOR EFFECTING DORSAL VEIN LIGATION AND TUBULAR ANASTOMOSIS AND LAPAROSCOPIC PROSTATECTOMY

BACKGROUND OF THE INVENTION

The present invention is in the field of surgical apparatus and methods and is more specifically directed to apparatus and methods for effecting ligation of the deep dorsal venous complex using a transurethral approach and a vesico-urethral anastomosis using a mechanical stapling procedure which avoid the shortcomings of the prior known procedures for such operations. The invention is also intended for general use in tubular anastomosis.

Our prior U.S. Pat. Nos. 4,848,367 and 4,873,977, which are incorporated herein by reference, respectively describe a method of effecting dorsal vein ligation and a stapling method and apparatus for vesicle-urethral re-anastomosis using an inflatable anvil assembly 2 which is inserted through the patient's urethra. Dorsal vein ligation is effected by inflating the inflatable bladder 80 of the anvil assembly 23 while it is in the urethra to radially distend the urethra against the dorsal vein to effect substantial compressive closure of the vein, and then ligating and transecting the dorsal vein. Stapling is effected using a circular female connector component 26 which is carried by the anvil assembly 23. Female connector component 26 is aligned with a circular male connector component 28 carried by a connector actuator 32, alignment being maintained by the inflation of anvil assembly 23. Male connector component 28 is then driven into mating engagement with female connector component 26 by actuator 32.

While the methods and apparatus disclosed in our prior patents provide satisfactory results, problems remain. For example, once compressive closure of the dorsal vein is effected in accordance with the method disclosed in U.S. Pat. No. 4,848,367, suturing of the dorsal vein must still be done in a "blind" area, making it difficult to position the ligating suture optimally with respect to the apical urethral sphincter. Also, the anastomosis effected by female and male connector components 26 and 28 is shorter and narrower than would be optimally desirable, and thus does not fully prevent bladder neck stenosis and urethral stricture.

SUMMARY OF THE INVENTION

The present invention overcomes the aforementioned problems left unsolved by our prior methods and apparatus through the provision of a ligator assembly comprising a hollow, bullet-shaped case and first and second suture needles carried by the case and a suture affixed to the first and second needles, the case having a proximal end and a distal end and dimensioned to be inserted in and through the body member said distal end of said hollow case being smoothly rounded and having a substantially transverse slot therein and drive mean for remotely driving the first and second needles longitudinally out of the case through the slot. The case comprises a cylindrical body and a rounded-end tip which are selectively separable. The proximal end of the case includes selectively operable second connection-permitting means operable to connect the case to an elongated tubular sound for placement of the ligator assembly. The interior surface of the case also is provided with first and second guide tubes for retaining and guiding the first and second needles, respectively. Guide means such as first and second wires engage the ends of the first and second needles to drive them out of the guide tubes and through the slot.

In order to effect ligation of a vein adjacent a hollow, tube-like body member using the ligator assembly according to the invention, the ligator assembly is inserted into the hollow tube-like body member, the case is positioned generally adjacent the vein to be ligated, the first and second needles are driven out through the slot, and through the wall of the hollow, tube-like body member on either side of the vein to be ligated, and a suture is formed around the vein to be ligated using the suture.

Apparatus for effecting an anastomosis according to the invention comprises female and male connector components usable with an operator, an inflatable anvil assembly, and a connector actuator substantially as described in U.S. Pat. Nos. 4,848,367 and 4,873,977, and which include mutually facing clamping surfaces for clamping generally annular tissue portions of the first and second body members together. The female connector component includes a plurality of resilient legs extending upwardly to the clamping surface thereof and a plurality of bores, each of the bores extending through the clamping surface and one of the resilient legs. The legs are movable between a retracted position when the inflatable anvil is contracted and a distended position when the anvil is expanded. The female connector component further includes an annular base, wherein the legs extend unitarily upwardly from the base. Each of the legs has an inner surface having an upper portion and a lower portion, the lower portion extending inwardly from the base to form an obtuse angle with the base when the leg is in the retracted position and to substantially align with the base when the leg is in the distended position. The male connector component includes a plurality of post means for piercing the annular tissue portions in response to actuation of the connector actuator and for matingly engaging the bores in the female connector component when the legs are in the distended position.

Thus it is a object of the invention to provide a method and apparatus which permits ligation of the deep dorsal venous complex in a manner which reduces excessive blood loss and therefore reduces intra and post-operative morbidity.

It is another object of the invention to provide a method and apparatus which permits performing an anastomosis in a manner which potentially minimizes long-term complications of bladder neck stenosis and urethral stricture.

It is still another object of the invention to provide apparatus for effecting dorsal vein ligation and tubular anastomosis which can be used to perform a prostatectomy laparoscopically.

A better understanding of the disclosed embodiments of the invention will be achieved when the accompanying detailed description is considered in conjunction with the appended drawings, in which like reference numerals are used for the same parts as illustrated in the different figures.

BRIEF DESCRIPTION OF THE DRAWINGS

FIG. 6 is a cross-sectional view taken along line 6—6 of FIG. 5;

FIG. 7 is an partial perspective view of a suture needle attached to a drive wire in accordance with the invention;

FIG. 8 is a side plan view of a suture needle according to the invention;

FIG. 9 is a front plan view of the eye of the needle of FIG. 8;

FIG. 10 is a front plan view of the eye of the needle of FIG. 9 having a suture crimped thereto;

FIG. 11 is a top plan view of a female connector component;

FIG. 12 is a side plan view of the female connector component of FIG. 11;

FIG. 13 is a cross-sectional view taken along line 13—13 of FIG. 11, in which the legs of the female connector component are in the retracted position;

FIG. 14 is a cross-sectional view of the female connector component in which the legs are in the distended position;

FIG. 15 is an exploded plan view of the female connector component and the inflatable anvil assembly;

FIG. 16 is a plan view of the female connector component assembled to the inflatable anvil assembly and aligned with a male connector component, prior to inflation of the anvil assembly;

FIG. 17 is a plan view of the male connector component in mating engagement with the female connector component, with the anvil assembly inflated;

FIG. 18 is a plan view of the male connector component in mating engagement with the legs of the female connector component, with the frame of the female connector component, the anvil assembly, and the reinforcing wires of the male connector componend removed.

DESCRIPTION OF THE PREFERRED EMBODIMENTS

Figure 1:
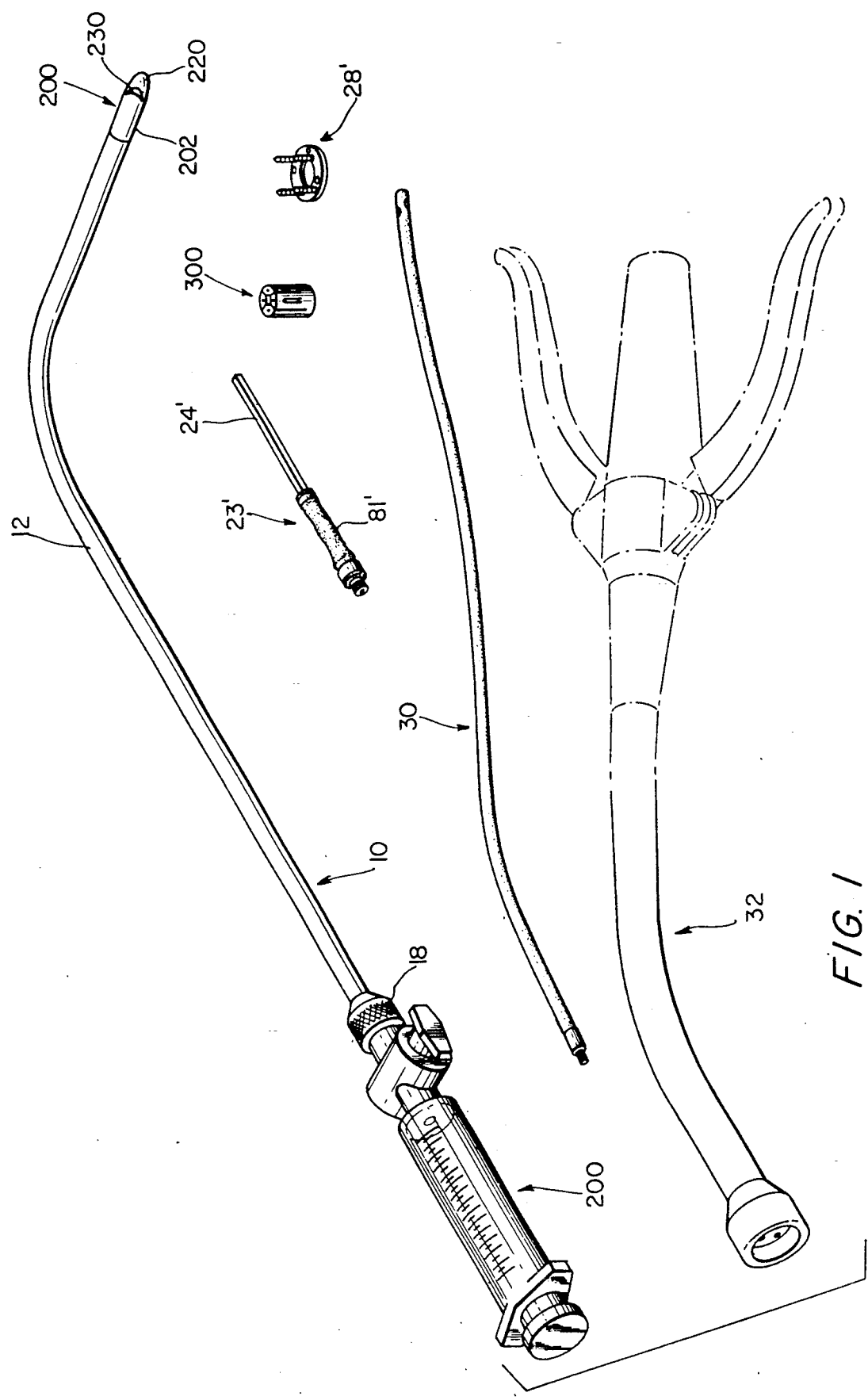
FIG. 1 is a perspective view of the separate components of the preferred apparatus used in the practice of the present invention.

Like reference numerals are used herein for the same parts as illustrated in our U.S. Pat. Nos. 4,848,367 and 4,873,977. Referring now to FIG. 1, there are shown the different parts of the invention in a pictorial manner and which includes seven major components, operator 10, dorsal vein ligator assembly 200, inflatable anvil assembly 23', female connector component 300, male connector component 28', catheter 30, and connector actuator 32.

Inflatable anvil assembly 23', illustrated in FIGS. 1 and 15-17, is generally similar to anvil assembly 23 described in U.S. Pat. Nos. 4,848,367 and 4,873,977, except that anvil assembly 23' is provided with an outer envelope 81' which is substantially cylindrical when uninflated. Anvil assembly 23' includes an elongated rigid hollow anvil core tube 24' also generally similar to anvil core tube 24 described in U.S. Pat. Nos. 4,848,367 and 4,873,977, except that that portion of anvil core tube 24' which is exterior to the outer envelope 81' has a square transverse cross-section, for a purpose to be described hereinafter.

Figure 4:
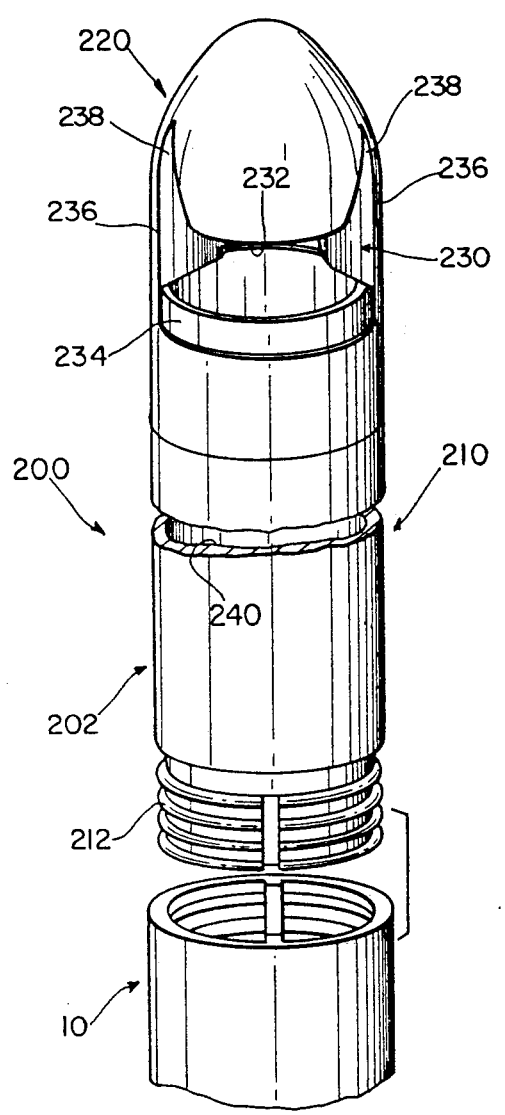
FIG. 4 is an enlarged perspective view of the ligator assembly of FIG. 3.
Figure 5:
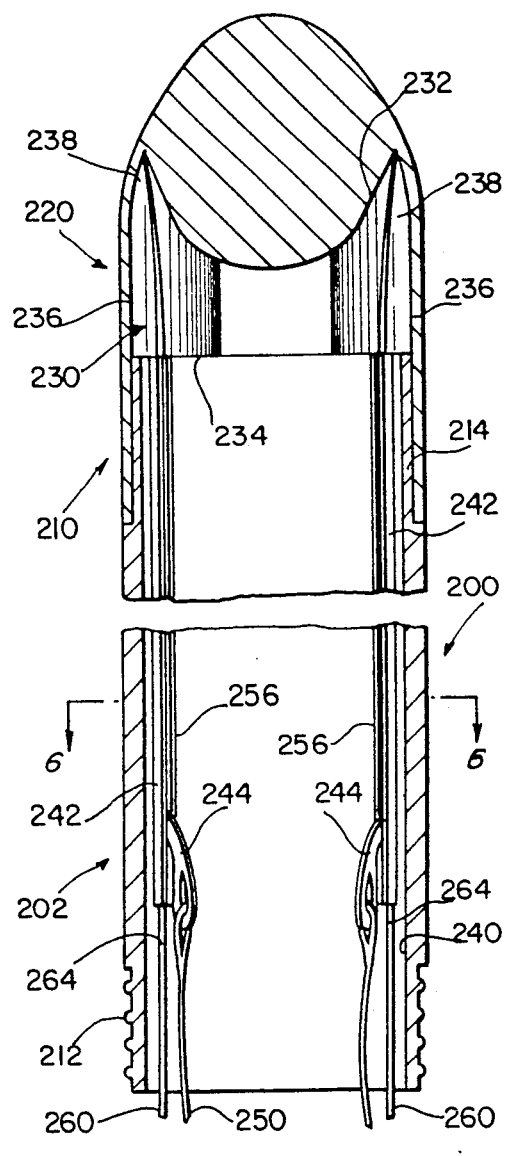
FIG. 5 is a cross-sectional view of the ligator of FIG. 3 as assembled to the tubular sound.

Dorsal vein ligator assembly 200 is used in place of rounded-end tip 14 described in U.S. Pat. Nos. 4,848,367 and 4,873,977. As shown in FIGS. 3-6, ligator assembly 200 comprises a bullet-shaped case having two parts, a hollow cylindrical body 202 having an inset, externally- threaded proximal end 212 and an inset, unthreaded distal end 214 (FIG. 5), and a rounded-end tip 220 having a proximal end 222 for selectively engaging distal end 214 of body 210 and a closed distal end 224. As shown in FIG. 5, distal end 214 of body 210 and proximal end 222 of tip 220 are held in engagement by a friction fit. However, any other suitable means can be used. Also, distal end 214 of body 210 and proximal end 22 of tip 220 can be provided with alignment means, such as a mating notch and slot (not shown) in order to ensure proper positioning of tip 220 on body 210.

Tip 220 is provided with an elongated transverse slot 230. As shown in FIGS. 4 and 5, slot 230 has a distal edge 232 which in longitudinal cross-section is substantially U-shaped, a proximal edge 234 which in longitudinal cross-section is substantially linear, and opposed side edges 236 joining the ends of distal and proximal edges 232 and 234. Notches 238 are defined the intersection of side edges 236 with distal edge 232.

Referring now to FIGS. 5 and 6, the interior wall 240 of body 210 is provided with a pair of spaced-apart, longitudinal and substantially linear guide tubes 242 dimensioned to receive a pair of suture needles 244 and guide them out of the case 202 through slot 230. Each of guide tubes 242 is placed at an angle of approximately 12° to 30° to the axis of body 210, so that needles 244 will exit slot 230 at a corresponding angle. Guide tubes 242 are placed in body 210 slightly inwardly of side edges 236 of slot 230, so that the points of suture needles 244 can rest in notches 238 prior to extrusion of suture needles 244; and further, when suture needles 244 are extruded from guide tubes 242, they will exit slot 230 at notches 238 where slot 230 is deepest.

The ends of a suture 250 are retained in suture needles 244 by eyes 252 formed at the proximal ends 254 of suture needles 244. As shown in FIGS. 5 and 6, eyes 252 can be positioned transversely of the longitudinal axes of suture needles 244. In order to accommodate eyes 252, guide tubes 242 can be provided with longitudinally extending channels 256 which open into the interior of body 210 and in which eyes 252 can slidably travel.

Figure 3:
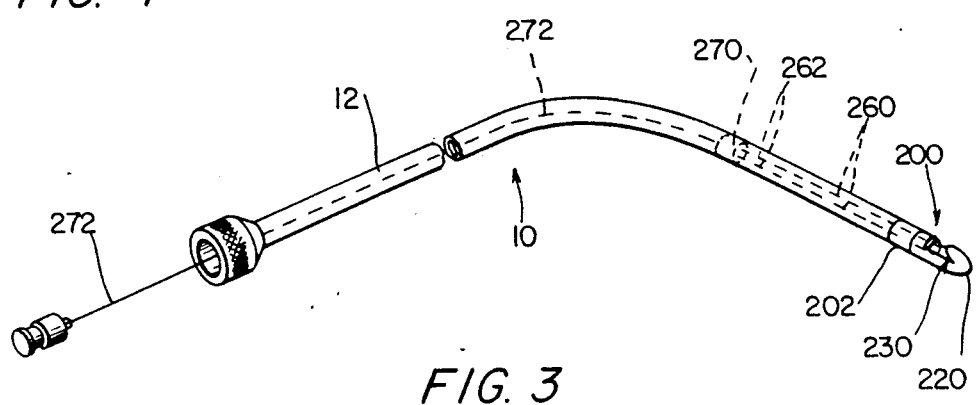
FIG. 3 is a perspective view of the ligator assembly according to the invention, assembled with an elongated tubular sound.

Preferably, suture needles 244 are extruded simultaneously from case 202. As shown in FIGS. 3, 5, and 7, suture needles 244 are driven by a pair of resilient and flexible drive wires 260 dimensioned to be inserted into guide tubes 242 and having proximal ends 262 and distal ends 264. At their distal ends 264, drive wires 260 are provided with means such as fingers 266 (FIG. 7) for selectively gripping the proximal ends 254 of suture needles 244 adjacent eyes 248. As shown in FIG. 3, the proximal ends 262 of wires 260 are received in a piston 270 which is slidably received in hollow sound 12 and reciprocated by a single drive wire 272.

Alternatively, suture needles 244 can be extruded individually from case 202. In that case, suture needles 244 can be driven directly by wires 260 without the intermediary of piston 270 and wire 272.

Suture needles 244 can easily be loaded into their respective guide tubes 242 by removing tip 220 from case 202. The proximal ends 254 of suture needles 244 are inserted into guide tubes 242 a sufficient distance to allow the points 274 to rest on respective notches 238 of slot 230. After suture needles 244 are loaded, drive wires 260 are engaged and case 202 is threaded onto the end of sound 12.

Referring now to FIGS. 11-14, female connector component 300 is unitarily formed from a substantially cylindrical block of flexible and resilient material and comprises a frame 302 carrying a plurality of resilient legs 304 movable between a retracted position (FIG. 13) and a distended position (FIG. 14. Frame 302 comprises an annular base 310, a top 312, and a plurality of spaced-apart longitudinal columns 314 (FIGS. 12 and 15-18) extending between base 310 and top 312. Legs 304 extend unitarily upwardly from base 310 between columns 314. As shown in FIG. 11, in plan view, top 312 has the form of a cross in which the ends of the arms 320 are flared outwardly and have rounded edges and the center is provided with a square aperture 330 therethrough for matingly engaging core tube 24'.

Each of legs 304 has an outer surface 340, an inner surface 342, a pair of side surfaces 344 (FIG. 11) joining outer and inner surfaces 340 and 342, and an upper surface 346. Outer surfaces 340 are coextensive with the outer surface of female connector component 300. Upper surfaces 346 angles downwardly towards aperture 330 when legs 304 are in the retracted position (FIG. 13), so that when legs 304 are in the distended position, upper surfaces 346 are substantially perpendicular to the longitudinal axis of female connector component 300 (FIG. 14). Upper surfaces 346 in conjunction with top 312 of frame 302 define a clamping surface for clamping an annular portion of tissue.

As shown in FIGS. 13 and 14, each inner surfaces 342 has an upper portion 350 and a lower portion 352. The lower portion 352 of each inner surfaces 342 extends inwardly from base 310 to form an obtuse angle with base 310 when the leg 304 is in the retracted position (FIG. 13) and to extend substantially parallel to the longitudinal axis of female connector component 300 when the leg 304 is in the distended position (FIG. 14). The upper portion 350 of inner surface 342 extends longitudinally from upper surface 346. Upper and lower portions 350 and 352 of each inner surface 342 are separated by an angular notch 360, the upper surface 362 of which is substantially perpendicular to the longitudinal axis of female connector component 300 when leg 304 is in the retracted position, to facilitate correct positioning of leg 304 in the distended position.

A cylindrical bore 370 extends through each of legs 304, the longitudinal axis of bore 370 being parallel to the lower portion 352 of the inner surface 342. Thus, when legs 304 are in the distended position, bores 370 are substantially parallel to the longitudinal axis of female connector component 300 (FIG. 14).

As shown in FIGS. 13 and 14, the inner surfaces 342 of legs 304 and the inner surfaces 380 of columns 314 define an interior cavity 382 in female connector component 300 for receiving inflatable anvil assembly 23'.

Referring now to FIG. 16, male connector component 28' is generally similar to male connector component 28 described in U.S. Pat. Nos. 4,848,367 and 4,873,977, except that male connector pins 66' of male connector component 28' are longer and narrower to matingly engage cylindrical bores 370 in female connector component 300, which are longer and narrower than the female connector socket tubes 46 of female connector component 28. Also, male connector pins 66' are provided with strengthening wires 66" therein, which provide added rigidity to male connector pins 66'.

Male and female connector components 28' and 300 are both preferably made of a biosoluble material which eventually dissolves in the human body, such as the soluble suture material manufacture by Ethicon, Inc. of Somerville, N.J. Other biosoluble polymers that may be used for components 28' and 300 are disclosed in U.S. Pat. Nos. 3,297,033; 3,463,158; 3,597,449; 3,620,218; and 3,875,937.

Figure 2A:
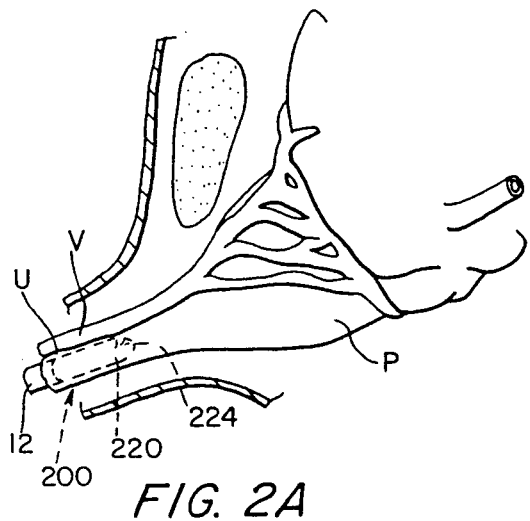
FIG. 2A is a perspective view of the human prostate, bladder and associated organ illustrating an initial step in practive of the invention by the preferred embodiment thereof.
Figure 2B:
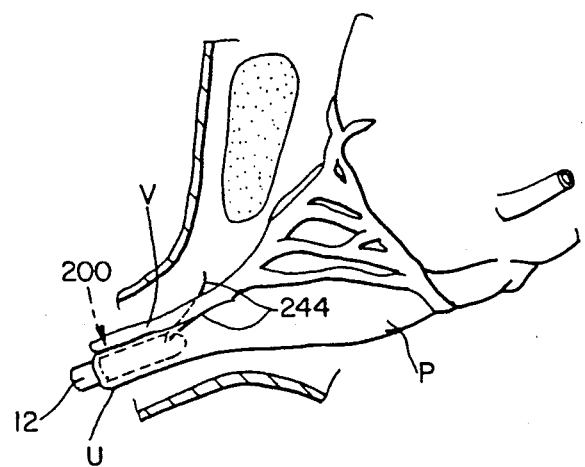
FIG. 2B illustrates a step subsequent to that of FIG. 1A in the practice of the inventive method.
Figure 2C:
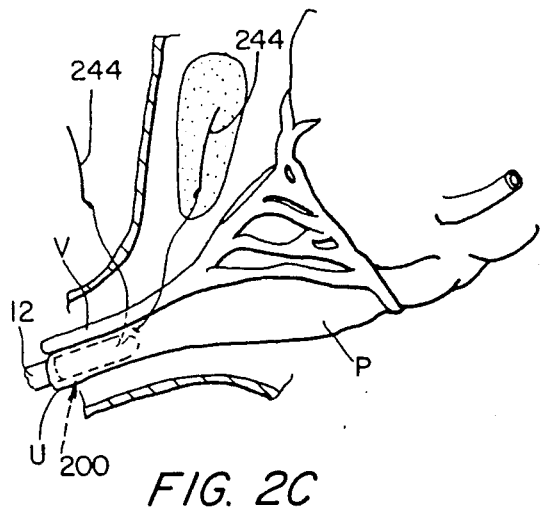
FIG. 2C illustrates a step subsequent to the step of FIG. 2B in the inventive method.
Figure 2D:
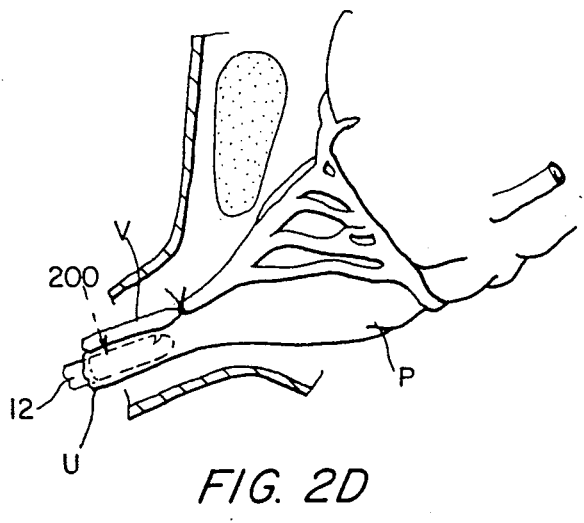
FIG. 2D illustrates a step subsequent to that of FIG. 2C.
Figure 2E:
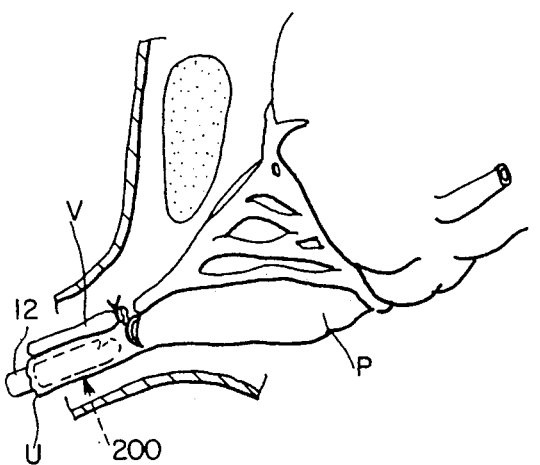
FIG. 2E illustrates a step subsequent to that of FIG. 2D.
Figure 2F:
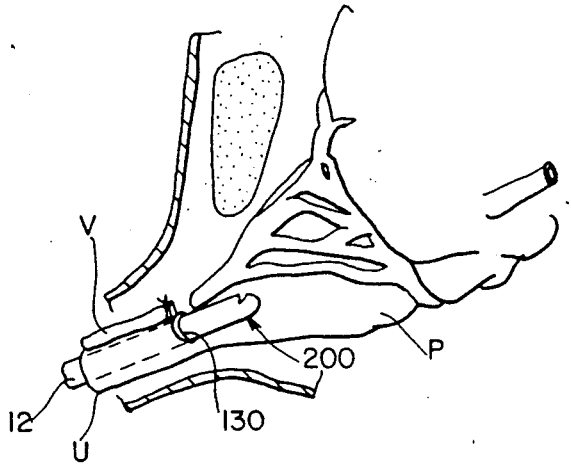
FIG. 2F illustrates a step subsequent to that of FIG. 2E.

The manner of using the inventive veinous ligator apparatus will now be discussed with reference being made to FIGS. 2A-2F. As described in U.S. Pat. Nos. 4,848,367 and 4,873,977, the urethral sound 12 is inserted through the urethra U to a position substantially as shown in FIG. 2A. The distal end 224 of tip 220 of ligator assembly 200 will extend into the apex of the prostate P, immediately under the dorsal vein V. As shown in FIGS. 2B and 2C, suture needles 244 are then extruded through the urethra U on either side of the dorsal vein V. Use of the ligator assembly 200 permits the ligating suture to be reliably place in close proximity to the apical urethral sphincter without compromising it. The dorsal vein V is ligated as shown in FIG. 2D and transected as shown in FIG. 2E, and an initial urethrotomy 130 is then provided in the urethra U, of sufficient size to permit ligator assembly 200 and urethral sound 12 to be pushed outwardly through the urethrotomy 130, as shown in FIG. 2F; however, the urethra is not completely transected at this time, but later, as described in U.S. Pat. Nos. 4,848,367 and 4,873,977. Ligator assembly 200 and drive wires 260, piston 270, and drive wire 272 are then removed from sound 12 and are not of any further use in the procedure.

Piston-cylinder means 20 (FIG. 1) can then be connected to connector 18 of sound 12, and deflated inflatable anvil assembly 23' with female connector component 300 mounted thereon can then be threaded into threaded socket 13 of inflatable anvil assembly 23', as described in U.S. Pat. Nos. 4,848,367 and 4,873,977. The procedure continues as described in U.S. Pat. Nos. 4,848,367 and 4,873,977, except that female connector component 300 of the present invention is substituted for female connector component 26.

The manner of using the inventive anastomosis apparatus will now be discussed with reference being made to FIGS. 15-18. Only the forward portion of anvil assembly 23' is inserted into cavity 382 of female connector component 300. The rearward portion of anvil assembly 23' protrudes outwardly from female connector component 300. Inflation of the rearward portion of inflatable anvil assembly 23' causes the apical urethra to expand to its widest functional diameter. The forward portion of anvil assembly 23' expands against inner surfaces 342 of legs 304 of female connector component 300, and more particularly, against the inwardly angled lower portions 352 thereof. Legs 304 will then assume their distended positions with cylindrical bores 370 in axial alignment with male connector pins 66'. The increased length and width of female connector component 300, in combination with expansion of the apical urethra, are effective in preserving both full patency of the bladder neck and functional urethral length, thus preventing bladder neck stenosis and urethral stricture.

As further described in U.S. Pat. Nos. 4,848,367 and 4,873,977, the sides of the opening in the bladder are sutured, actuator 32 is actuated to cause male connector pins 66' to penetrate the bladder and urethral tissue and lockingly engage bores 370 of female connector component 300, and to activate a circular blade 120. In addition, legs 304 are separated from frame 302 of female connector component 300 by severing legs 304 where they join base 310, thus allowing withdrawal of frame 302 with inflatable anvil assembly 23'; and strengthening wires 66" are removed from male connector pins 66'. Severing of legs 304 from frame 302 can be accomplished using a laser or other conventional cutting means. If a laser is used, the areas to be cut are conventionally treated to absorb the laser light, leaving the remaining areas unaffected by the laser. The procedure is then concluded as in described in U.S. Pat. Nos. 4,848,367 and 4,873,977.

The apparatus according to the invention for effecting dorsal vein ligation and tubular anastomosis can be used in combination with commercially available trocar which have been modified in a conventional manner in order to perform a prostatectomy laparoscopically, as will now be described.

Figure 19:
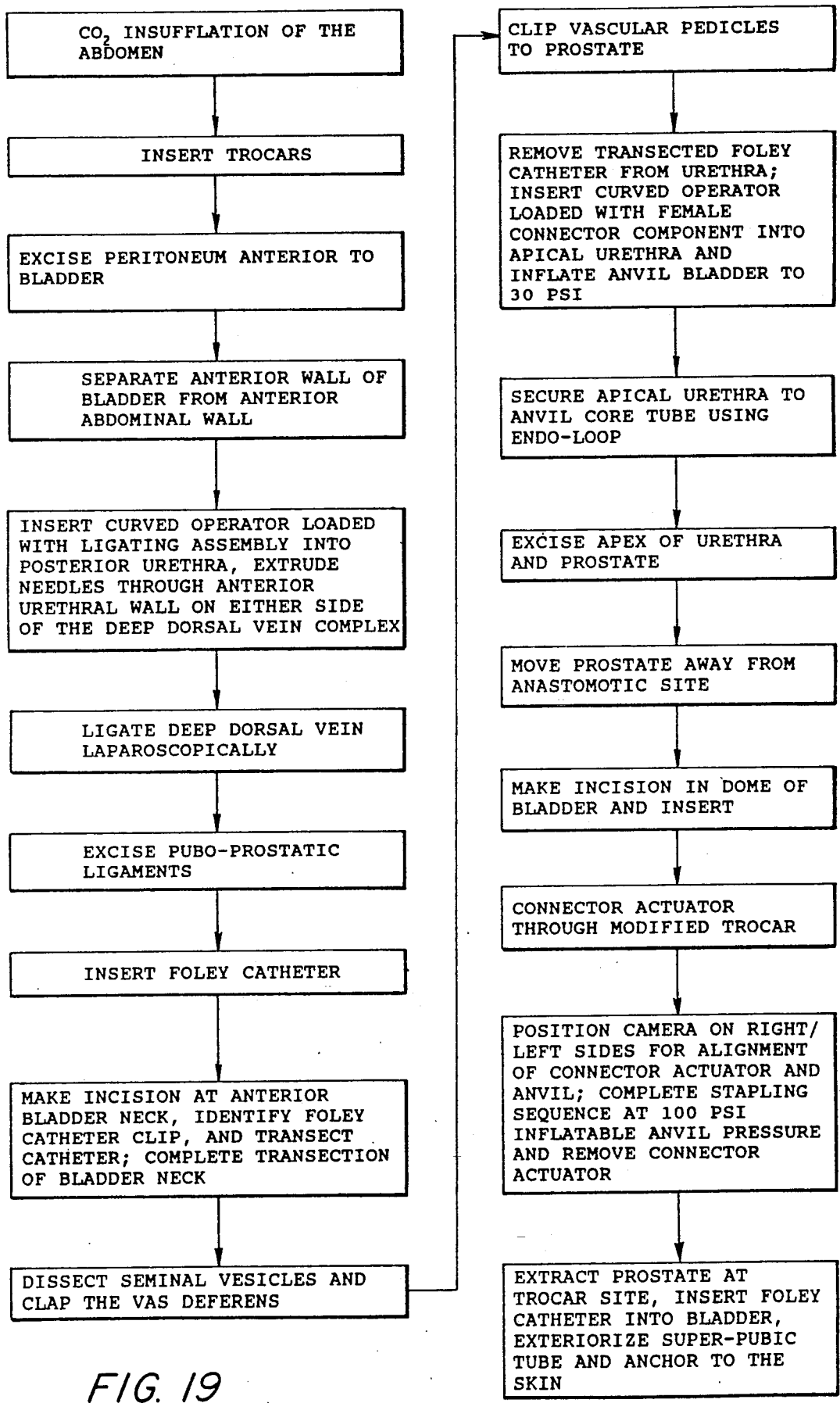
FIG. 19 is a flow chart describing a procedure for performing a prostatectomy laparoscopically using the apparatus according to the invention.

For this procedure, a commercially-available trocar, such as the Karl Storz single puncture trocar, model #26020 AS, are employed, one of which is modified in a conventional manner using a reducing sleeve to have a 17 mm. inner diameter. Referring to FIG. 19, the abdomen is insufflated with $CO_2$. Three trocars are inserted, two small lateral ports and one 17 mm. umbilical port. Following dissection of the nodes laparoscopically, as described by Drs. Schuessler and Vancaille, the peritoneum is excised in conventional fashion anterior to the bladder with a KTP 532 laser or scissors. The anterior wall of the bladder is likewise conventionally separated from the anterior abdominal wall.

The curved operator 10 with dorsal vein ligator assembly 200 attached is inserted into the posterior urethra, and suture needles 244 are extruded as previously described through the anterior urethral wall on either side of the deep dorsal venous complex proximal to the striated sphincter. The deep dorsal vein is then ligated laparoscopically.

Following ligation of the deep dorsal vein, the puboprostatic ligaments are excised in conventional fashion. A Foley catheter is inserted into the urethra. An incision is made at the anterior bladder neck, following which the Foley catheter clip is identified and the catheter is transected using the stem for anterior traction of the bladder, also all in conventional fashion. Transection of the bladder neck is completed by excising the posterior bladder wall at the juncture of the prostate to the bladder neck. It is noted that prior to transection of the catheter and bladder neck, previously-prepared Flourescen-tagged prostatic monoclonal antibody is directly injected into the hypogastric artery, which was exposed during the prior laparoscopic node dissection.

The seminal vesicles are dissected and the vas deferens clamped. The vascular pedicles are then clipped adjacent to the prostate.

At this stage, the transected Foley catheter is removed from the urethra. Curved operator 10 loaded with inflatable anvil assembly 23' and female connector component 300 is inserted as previously described in the apical urethra, the anvil assembly 23' and female connector component 330 being covered by a protective rubber cap (not shown) to hold legs 304 of female connector component 330 in their retracted position and provide a smooth surface to permit insertion of female connector component 330 and anvil assembly 23' into the apical urethra. The inflatable bladder of inflatable anvil assembly 23' is inflated to 30 psi. The cap is then removed from the fastener female connector component 330.

The apical urethra is secured to anvil core tube 24' using an endo-loop as described in our prior U.S. Pat. Nos. 4,848,367 and 4,873,977. The apex of the urethra and prostate are then excised using a laser, and the prostate is moved away from the anastamotic site.

After the prostate is moved away, an incision is made in the dome of the bladder and connector actuator 32 loaded with male connector component 28' is inserted through the modified 17 mm. port of the trocar.

A conventional laparoscopic camera, for example the Karl Storz 10 mm. intraoperative camera, is positioned on the right or left port as appropriate for alignment of actuator 32 and anvil assembly 23'. The stapling sequence is then completed at a pressure of approximately 100 psi in the inflatable bladder of anvil assembly 23', as previously described, and actuator 32 is removed, also as previously described.

Finally, the prostate is extracted at the single puncture trocar sight. A Foley catheter is inserted into the bladder, and the super-pubic tube is exteriorized and anchored to the patient's skin.

While the preferred embodiments of the invention are directed to prostate removal, it should be understood that the spirit and scope of the invention are not limited to prostate operations. In fact, the inventive apparatus and method can be used for ligating other veins and for joining other tubular body parts.

What is claimed is:

1. Apparatus for effecting ligation of a vein adjacent a hollow, tube-like body member, comprising:
    a hollow bullet-shaped sound dimensioned to be inserted in and through a tube-like body member and having a hollow, cylindrical body and a rounded-end tip, said body having an interior wall and a longitudinal axis and said tip having an elongated transverse slot therein; and
    first and second spaced-apart, substantially linear needle guide means positioned on said interior wall for longitudinally guiding first and second needles, respectively, from inside said hollow sound out through said transverse slot.

2. The apparatus of claim 1, said first and second needle guide means comprising first and second guide tubes, respectively.

3. The apparatus of claim 2, further comprising first and second suture needles for positioning inside said first and second guide tubes and a suture having first and second ends respectively attached to said first and second needles.

4. The apparatus of claim 3, said suture needles each having an eye extending laterally therefrom, and said first and second guide tubes each having a longitudinal channel therein facing into the interior of said body for slidably receiving said eyes.

5. The apparatus of claim 1, further comprising:
   first and second suture needles slidably received within said first and second needle guide means, respectively; and
   drive means for remotely driving said first and second needles in said first and second needle guide means, respectively and for extruding said first and second suture needles out through said transverse slot.

6. The apparatus of claim 5, said drive means including first and second flexible and resilient drive wires dimensioned to be inserted into said first and second guide means, respectively, said first and second drive wires respectively engaging said first and second needles.

7. The apparatus of claim 6, wherein said drive means drive said first and second needles simultaneously.

8. The apparatus of claim 6, wherein said drive means drives said first and second needles individually.

9. The apparatus of claim 2, wherein said first and second guide tubes are at an angle to said longitudinal axis of said sound.

10. The apparatus of claim 9, wherein each of said first and second guide tubes is at an angle of approximately 12° to 30° to said longitudinal axis of said sound.

11. A surgical apparatus for effecting the ligation of a vein adjacent a hollow, tube-like body member comprising:
   (a) an operator comprising an elongated hollow tube having a proximal end and a distal end and dimensioned to be inserted in and through said body member to position said distal end generally adjacent the vein to be ligated and including selectively operable first connection-permitting means provided in said distal end;
   (b) a tip component comprising a hollow bullet-shaped case and first and second suture needles carried by said case, said case having a proximal end and a distal end and dimensioned to be inserted in and through the body member and including selectively operable second connection-permitting means provided in said proximal end operable for engagement with said first connection-permitting means for connecting said tip component to said distal end of said elongated hollow tube, said distal end of said hollow case being smoothly rounded and having a substantially transverse slot therein; and
   (c) drive means for remotely driving said first and second needles longitudinally out of said case through said slot.

12. A method for effecting ligation of a vein adjacent a hollow, tube-like body member, comprising the steps of:
   inserting into the hollow tube-like body member a bullet-shaped hollow sound dimensioned to be inserted in and through the tube-like body member, the hollow sound having a longitudinal axis, an open end, a closed, smoothly-rounded end, a substantially transverse slot in said rounded end, first and second suture needles longitudinally movable inside the hollow sound and aligned with the transverse slot, and a suture having first and second ends respectively attached to the first and second needles;
   positioning the hollow sound generally adjacent the vein to be ligated;
   driving the first and second needles out through the slot, and through the wall of the hollow, tube-like body member on either side of the vein to be ligated; and
   forming a suture around the vein to be ligated using the first and second sutures.

13. A surgical apparatus for effecting the connection of first and second hollow body members comprising:
   (a) female and male connector components;
   (b) a first operator comprising an elongated hollow tube having a distal end and dimensioned to be inserted in and through the first body member to position said distal end generally adjacent a part of the first body member to be joined to the second body member and including selectively operable first connection permitting means provided in said distal end;
   (c) anvil means dimensioned to be positionable in said first body member and including second connection permitting means operable for engagement with said first connection permitting means for connecting said anvil means to said distal end of said elongated hollow tube and further including first alignment means spaced from said second connection permitting means and a female connector component supporting means for supporting said female connector component, said anvil means being selectively expandable and contractible;
   (d) a second operator including a tubular housing having a distal end and being dimensioned to be positionable in the second body member with its distal end adjacent a portion of the second body member to be joined to the first body member, a male connector component supporting means in said distal end for supporting said male connector component, and second alignment means engageable with said first alignment means of said anvil means for effecting proper alignment of said female and male connector components in a ready condition and force exerting movable means mounted for movement in said tubular housing toward said anvil means when said first and second alignment means are in said ready condition, for forcefully moving said male connector component toward said female connector component to effect locking engagement of said female and male connector components; and
   (e) wherein said female and male connector components include mutually facing clamping surfaces for clamping generally annular tissue portions of the first and second body members together when said second alignment means is engaged with said first alignment means and wherein said female connector component includes a plurality of resilient legs extending upwardly to said clamping surface thereof and a plurality of bores, each of said bores extending through said clamping surface and one of said resilient legs, and wherein said legs are movable between a retracted position when said anvil means is contracted and a distended position when said anvil means is expanded, and wherein said male connector component includes a plurality of post means for piercing said annular tissue portions in response to actuation of said force exerting means and for matingly engaging said plurality of bores in said female connector component when said legs are in the distended position, and wherein said post means and said bores hold said annular tissue portions in clamped engagement with each other following locking engagement of said female and male connector components.

14. The apparatus of claim 13, wherein said female connector component further includes an annular base, wherein said legs extend unitarily upwardly from said base and wherein each of said legs of said female connector component has an inner surface having an upper portion and a lower portion, said lower portion extending inwardly from said base to form an obtuse angle with said base when said leg is in the retracted position and to substantially align with said base when said leg is in the distended position.

15. The apparatus of claim 13, wherein said post means have outward protrusion means for preventing withdrawal of said post means after positioning thereof in said bores.

16. The apparatus of claim 13, wherein the first body member comprises the human male urethra and the second body member comprises the human male bladder, and said elongated hollow tube, said anvil means, and said female connector component are dimensioned so as to be receivable in the human male urethra.

17. A surgical apparatus for effecting the connection of first and second hollow body members comprising female and male connector components, said female and male connector components include mutually facing clamping surfaces for clamping generally annular tissue portions of the first and second hollow body members together, wherein said female connector component includes a plurality of resilient legs extending upwardly to said clamping surface thereof and a plurality of bores, each of said bores extending through said clamping surface and one of said resilient legs, and wherein said legs are movable between a retracted position and a distended position, and wherein said male connector component includes a plurality of post means for piercing the annular tissue portions and for matingly engaging said plurality of bores in said female connector component when said legs are in the distended position, and wherein said post means and said bores hold said annular tissue portions in clamped engagement with each other following locking engagement of said female and male connector components.

18. The surgical apparatus of claim 17, further comprising:
a first operator having a distal end and dimensioned to be inserted in and through said first body member to position said distal end generally adjacent a part of the first hollow body member to be joined to the second hollow body member;
anvil means dimensioned to be positionable in the first hollow body member and including a female connector component supporting means for supporting said female connector component, said anvil means being selectively inflatable to hold said female connector component in fixed position and distend the legs thereof;
selective connection means for selectively connecting said anvil means to said distal end of said first operator;
a second operator having a distal end and being dimensioned to be positionable in the second hollow body member with said distal end thereof adjacent a portion of the second hollow body member to be joined to the first hollow body member, a male connector component supporting means in said distal end thereof for supporting said male connector component, and actuator means for forcefully moving said male connector component toward said female connector component; and
alignment means for effecting proper alignment of said female and male connector components in a ready condition, wherein said actuator means moves said male connector component toward said female connector component when said alignment means is in said ready condition to effect locking engagement of said female and male connector components.

19. The surgical apparatus of claim 17, wherein said female connector component further includes an annular base, wherein said legs extend unitarily upwardly from said base and wherein each of said legs of said female connector component has an inner surface having an upper portion and a lower portion, said lower portion extending inwardly from said base to form an obtuse angle with said base when said leg is in the retracted position and to substantially align with said base when said leg is in the distended position.

20. The apparatus of claim 17, wherein the first hollow body member comprises the human male urethra and the second hollow body member comprises the human male bladder, and said elongated hollow tube, said anvil means, and said female connector component are dimensioned so as to be receivable in the human male urethra.

21. A method for effecting a laparoscopic prostatectomy, comprising the steps of:
insufflating the abdomen of the patient;
inserting three trocars into the patient, two small lateral ports and one umbilical port;
inserting a curved operator into the posterior urethra, the curved operator being provided at its distal end with a sound having a pair of suture needles therein;
extruding the suture needles through the anterior urethral wall on either side of the deep dorsal venous complex;
ligating the deep dorsal vein laparoscopically using the suture needles;
inserting the curved operator provided with a inflatable anvil at its distal end into the apical urethra, the inflatable anvil having a hollow core tube extending therethrough and a female connector component seated thereon;
partially inflating the inflatable anvil;
securing the apical urethra to the core tube of the inflatable anvil;
excising the apex of the urethra and the prostate;
inserting a connector actuator through the umbilical trocar, the connector actuator having a male connector component seated on the distal end thereof;
aligning the connector actuator with the inflatable anvil using a laparoscopic camera; and
actuating the connector anvil and fully inflating the inflatable anvil to engage the male and female connector components to effect an anastomosis of the bladder and the urethral tissue.

* * * * *

UNITED STATES PATENT AND TRADEMARK OFFICE
CERTIFICATE OF CORRECTION

PATENT NO. : 5,047,039

DATED : September 10, 1991

INVENTOR(S) : Odis L. Avant; Duane A. Crawford

It is certified that error appears in the above-identified patent and that said Letters Patent is hereby corrected as shown below:

>     column 10, line 10, "sutures" should be deleted
>     and --needles-- should be inserted in place
>     thereof.

Signed and Sealed this

Twenty-first Day of December, 1993

Attest:

BRUCE LEHMAN

*Attesting Officer*  *Commissioner of Patents and Trademarks*